United States Patent [19]
Polen et al.

[11] Patent Number: 5,226,326
[45] Date of Patent: Jul. 13, 1993

[54] VIBRATION CHAMBER

[75] Inventors: William E. Polen, Cincinnati; Jerry Schlagheck, West Chester, both of Ohio

[73] Assignee: Environmental Stress Screening Corp., Cincinnati, Ohio

[21] Appl. No.: 709,589

[22] Filed: May 31, 1991

[51] Int. Cl.$^5$ .............................................. G01N 29/00
[52] U.S. Cl. ........................................ 73/571; 73/579; 73/584
[58] Field of Search ................ 73/571, 579, 584, 586, 73/662, 663; 324/513

[56] References Cited

U.S. PATENT DOCUMENTS

| | | |
|---|---|---|
| 2,166,838 | 7/1939 | Anderson . |
| 2,716,887 | 9/1955 | Smith ............................ 73/579 |
| 3,104,543 | 9/1963 | Kaminski ...................... 73/571 |
| 3,198,007 | 8/1965 | Overton ........................ 73/571 |
| 3,827,288 | 8/1974 | Fletcher et al. .............. 73/584 |
| 3,854,327 | 12/1974 | Felix ............................. 73/584 |
| 4,168,761 | 9/1979 | Pappanikolaou . |
| 4,716,764 | 1/1988 | Felix ............................. 73/571 |

OTHER PUBLICATIONS

H. H. Hubbard et al., "Vibration Induced by Acoustic Waves," in C. M. Harris et al., *Shock and Vibration Handbook* (New York, McGraw-Hill, 1961), pp. 48-46 to 48-55. TA 355 H 35.

"Methodology and Techniques of Environmental Stress Screening," 1988 by Jerry Schlagheck.

*Primary Examiner*—John E. Chapman
*Attorney, Agent, or Firm*—Frost & Jacobs

[57] ABSTRACT

A vibration chamber for screening or testing printed circuit boards by subjecting the printed circuit boards to acoustical vibrations which are generated by top and bottom speakers which face each other, with the printed circuit boards between the speakers. The top and bottom speakers are arranged in a "push-pull" configuration so that the speakers cooperate with one another in pushing air up and down in the vertical plane, thus imparting maximum acoustical energy to both sides (top and bottom) of the printed circuit board under test. The vibration chamber can be mated to a roller conveyor system for automatically running printed circuit boards through the vibration chamber in a production environment, and the speaker system can be driven by a profile of random vibration noise to achieve the maximum number of modes of vibration on the printed circuit board in the minimum amount of time.

22 Claims, 8 Drawing Sheets

VIBRATION CHAMBER
BLOCK DIAGRAM-ELECTRICAL CONNECTIONS

VIBRATION CHAMBER

TECHNICAL FIELD

The present invention relates generally to acoustical screening and test equipment, and is particularly directed to the screening and testing of components and assemblies, such as electronic printed circuit boards, which are susceptible to mechanical failure when subjected to conditions of vibration and shock. The invention will be specifically disclosed in connection with a "push-pull" speaker system that transfers energy to the components or assemblies being tested, from both above and below such components or assemblies.

BACKGROUND OF THE INVENTION

Acoustic test chambers have been known in the art for many years. For example, in U.S. Pat. No. 3,014,543 an Acoustical Vibration Test Device was disclosed which subjected devices under test to high sound pressure levels, and was specifically aimed at testing aircraft and missile components. This patent disclosed the fact that random noise could be used by varying the spectral distribution of the sounds produced. One limitation of the apparatus disclosed in that patent was the use of two chambers (an outer and an inner chamber), one (the inner) to contain the device under test and to confine the sound generated by a loudspeaker, and the other (the outer) to produce low frequency sound.

In another U.S. Pat. No. 3,198,007, an acoustic testing chamber was disclosed which subjected devices under test to high intensity acoustic vibrations, and was specifically aimed at testing guided missile or rocket components. This patent disclosed the use of two sound sources, one located on the longitudinal axis of the test chamber, and the other located on an axis 90° from the longitudinal axis. Also disclosed was the use of different frequency ranges produced by each of the two sound sources, and the use of an acoustical mirror to mix the sounds produced by the two sound sources and then direct such mixed sound onto the device under test.

In the electronics industry, a customary step of the manufacturing process is to assemble a printed circuit board with electrical and electronic components. Once the board is assembled, it is in a condition which lends itself to be tested, both mechanically and electrically. Typical mechanical tests that are performed on printed circuit boards at this stage of manufacture are sine wave vibration testing (typically at 2.2 g's at a non-resonant frequency or at a "swept" frequency) and temperature cycle testing (typically using thermal cycles from −40° F. to +160° F.). Such vibration testing does not simulate field operating conditions, nor does it act as an effective screening procedure by testing components under a wide range of non-resonant frequencies and g-forces.

The use of random vibration has been proven to be much more effective than the use of sine vibration. This is due to the presence of the entire frequency range. With sine vibration only one mode of vibration is excited at a time and only for a short period of time as the frequency is being swept. But with random vibration all the modes are excited. The premise is that random vibration screening is a cost saving both to the customer, in lower cost of ownership, and to the producer, in lower production costs. The key to the random vibration is the stimulation of the assembly maximizing the number of modes which can be excited during exposure to vibration. A final assembly which is well designed will minimize the number of modes and limit the displacement of the printed circuit assembly during exposure to vibration.

SUMMARY OF THE INVENTION

It is a primary object of the present invention to provide an acoustical screening, or testing, vibration chamber which imparts multiple modes of random vibration onto a device under test by the use of sound waves.

It is another object of the present invention to provide an acoustical vibration chamber which subjects a device under test to maximum g-force vibrations.

It is yet another object of the present invention to provide an acoustical vibration chamber which reduces resonance within the chamber to virtually nil, and which reduces the noise level which is created by the chamber around the exterior of the chamber to an acceptable amount for use within a factory environment.

Yet another object of the present invention is to provide an acoustical vibration chamber which produces a profile of random noise that is tailored to the particular device under test.

A still further object of the present invention is to provide an acoustical vibration chamber which works in cooperation with a conveyor system, so as to feed parts (devices under test) into and out of the chamber.

A yet further object of the present invention is to provide an acoustical vibration chamber which reduces the noise level created by the chamber around the exterior of the chamber, while at the same time works in cooperation with a conveyor system to feed parts into and out of the chamber.

It is still another object of the present invention to provide an acoustical vibration chamber which has means to hold the device under test in place, yet at the same time enable the device under test to vibrate in the axis of vibration without constraint.

It is a still further object of the present invention to provide an acoustical vibration chamber which imparts multiple modes of random vibration onto a device under test.

It is yet a further object of the present invention to provide an acoustical vibration chamber which uses speakers which face (oppose) each other to vibrate a device under test which is located between the speakers, and which provides suitable adjustability of distance between the device under test and the opposing speakers.

Additional objects, advantages and other novel features of the invention will be set forth in part in the description that follows and in part will become apparent to those skilled in the art upon examination of the following or may be learned with the practice of the invention. The objects and advantages of the invention may be realized and obtained by means of the instrumentalities and combinations particularly pointed out in the appended claims.

To achieve the foregoing and other objects, and in accordance with the purposes of the present invention as described herein an improved vibration chamber is provided having a plurality of speakers which are facing one another and may be axially aligned, and are electrically connected in opposite phases (by 180°) so as to operate in a "push-pull" arrangement. The push-pull arrangement operates to maximize the acoustical forces imparted onto a device under test, which is located between the speakers, by having the speakers "cooperate" with one another in pushing and pulling air against the device under test.

In accordance with a further aspect of the invention, the plurality of speakers are spaced apart from one another at the proper distance so as to impart the maximum g-force vibrations onto the device under test (without destroying the device under test), which is located between the speakers. If the speakers are aligned in the vertical plane, a minimum of one top and one bottom speaker is required, however, the invention operates equally as well with a plurality of top and bottom speakers which could be used to make up a much larger acoustical vibration chamber in order to vibrate much large parts. If more than one top speaker is used, all top speakers should be wired in parallel (in-phase). There should also be an equal number of bottom speakers, located in opposition and axially aligned to the top speakers, and all bottom speakers should be wired in parallel (in-phase), however, the top speakers as a group must be out-of-phase with the bottom speakers as a group.

According to a further aspect of the invention, sound deadening material is used to remove any resonance that might otherwise exist within the vibration chamber. The sound deadening material is placed on the interior surfaces of the chamber. In addition, a flexible material is used to cover the openings which are the entrance and exit access locations of the vibration chamber. This flexible material is chosen to also help dampen any interior resonance of the vibration chamber, and to help muffle the sounds that reach outside the vibration chamber.

In yet another aspect of the invention, electronic equipment is used to produce a profile of random noise (which is similar in characteristics to "white noise," but controlled over time) that is tailored to the particular device under test. A 1000-watt audio power amplifier (known in the prior art) is used to drive each speaker. The device that creates the profile of random noise is either a tape deck or a vibration controller (both are known in the prior art). The vibration controller must be able to produce random noise throughout the frequency range of 20 Hz to 2000 Hz, and it also must be able to notch out certain frequencies that must be determined for each type of device under test. The device under test will have certain resonant frequencies which are determined by using accelerometers on the device under test at low volume (low g-force amplitude) in the vibration chamber. Once those resonant frequencies are determined, they must be eliminated (notched-out) from the profile of random noise before full volume (high g-force amplitude) is used on the device under test. Once the profile is created, the sounds can be recorded on a tape deck, then later played back to any vibration chamber built according to this invention. The tape deck should have the ability to reproduce sounds over a frequency range of 20 to 2000 Hz, a dynamic range of approximately 40 dB, and a signal to noise ratio of at least 50 dB. If frequencies below 20 Hz are to be used in the profile of random noise, then a special tape deck that can record and play back such lower frequencies must be used. Frequencies greater than 2000 Hz can easily be re-created by standard tape decks. Note that the profile of random noise has an average distribution of amplitudes that are normalized (averaged) over a period of time (degrees of freedom) to a value expressed in $g^2Hz$. Unlike sine vibration, random vibration is measured in power (power spectral density-PSD). This measurement of power (PSD) is the area under the curve of the random profile in terms of overall $g_{rms}$. The RMS (root-mean-square) quantities are used due to the impossibility to measure a random signal in terms of peak magnitude. The curve for a typical profile is given in FIG. 1.

In a still further aspect of the invention, the vibration chamber has openings to allow a conveyor to feed parts through the vibration chamber. The openings can either be fitted with doors which close during vibration testing, or with flexible flaps that allow the device tested (e.g., a printed circuit board) to push its way through the flexible flaps. If flaps are used, they should have sound-deadening qualities.

In accordance with yet another aspect of the invention, the device under test is held in place during the vibration screening process along its edges only, so that it has freedom to vibrate up and down in the vertical axis without constraint. If a conveyor is used to move devices into the vibration chamber, it must be so designed as to not hold the device down, but only along the device's edge.

Still other objects of the present invention will become apparent to those skilled in this art from the following description wherein there is shown and described a preferred embodiment of this invention, simply by way of illustration, of one of the best modes contemplated for carrying out the invention. As will be realized, the invention is capable of other different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

The accompanying drawings incorporated in and forming a part of the specification illustrate several aspects of the present invention, and together with the description serve to explain the principles of the invention. In the drawings.

Reference will now be made in detail to the present preferred embodiment of the invention, an example of which is illustrated in the accompanying drawings.

DETAILED DESCRIPTION OF THE PREFERRED EMBODIMENT

Figure 2:
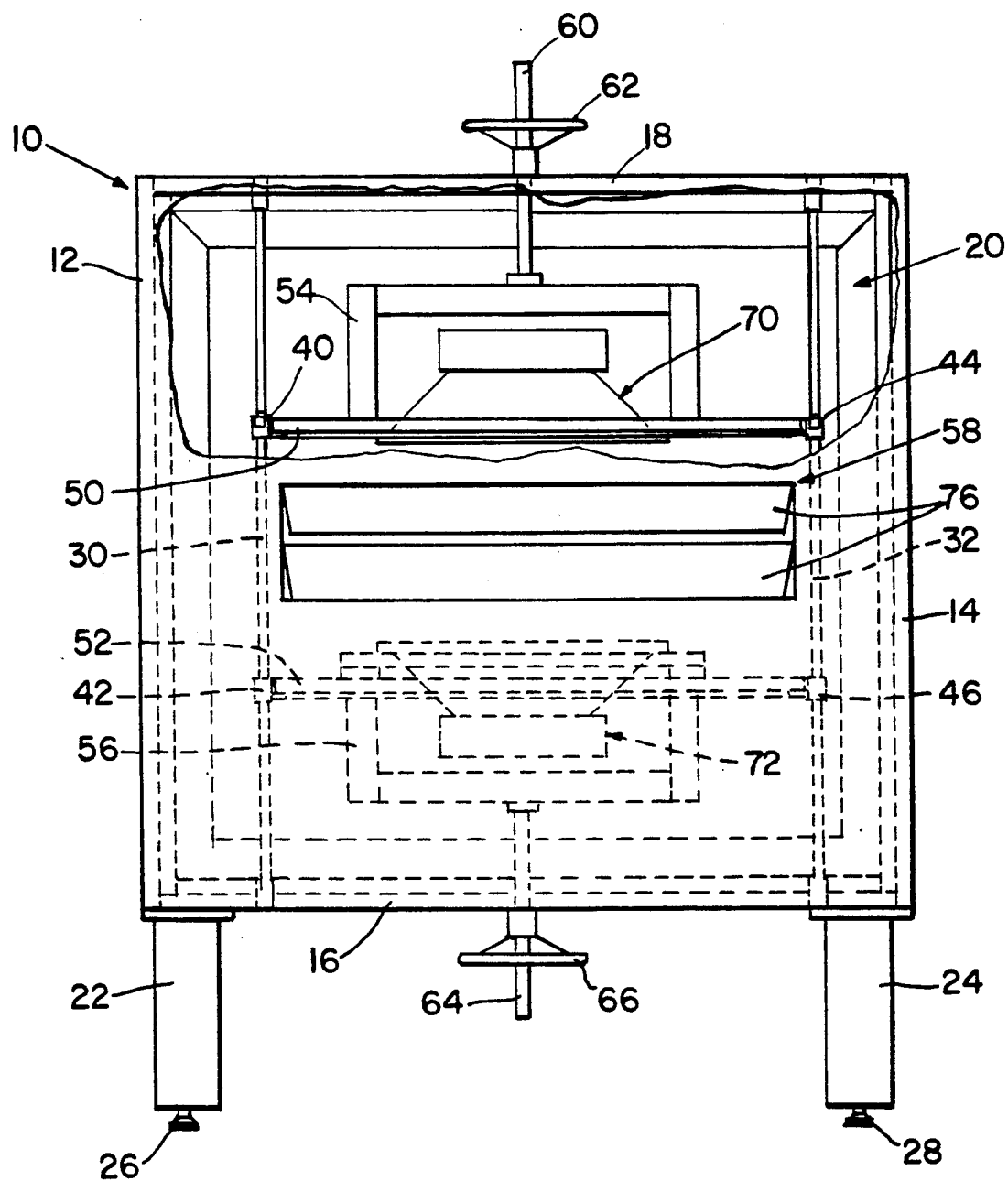
FIG. 2 is a front elevational view partially in cross-section of a vibration chamber constructed in accordance with the present invention.

Referring now to the drawings, FIG. 2 shows an acoustic vibration chamber, generally designated by the numeral 10, constructed in accordance with the principles of the present invention. In this embodiment, the vibration chamber is specifically made to test or screen printed circuit boards. FIG. 2 depicts a front view of such a vibration chamber, and shows a partial cut-away view showing some of the internal components.

In the illustrated embodiment of FIG. 2 the major points of construction of the acoustic vibration chamber are disclosed. The chamber is in the shape of a large box, having vertical walls 12 and 14, horizontal walls 16 and 18, along with vertical support legs 22 and 24 which sit upon leveling feet 26 and 28. Formed along the inner surfaces of the horizontal and vertical walls are layers of sound insulating and deadening materials 20.

The speakers of the illustrated embodiment of FIG. 2 can be adjusted up or down as per the requirements of the devices to be tested or screened. The top speaker 70 is mounted on a horizontal speaker support 50. This horizontal speaker support is in turn supported by the speaker support frame 54 which is attached to the top jack screw 60. The jack screw is actuated by the top jack screw adjustment 62. The horizontal speaker support 50 is attached to two speaker guides 40 and 44, which move up and down on the vertical guide rails 30 and 32. The bottom speaker 72 is mounted on the horizontal speaker support 52. This horizontal speaker support is in turn supported by the speaker support frame 56 which is attached to the bottom jack screw 64. The bottom jack screw is actuated by the bottom jack screw adjustment 66. The horizontal speaker support 52 is attached to two speaker guides 42 and 46 which move up and down on the vertical guide rails 30 and 32.

In the illustrated embodiment of FIG. 2 there are two speakers, one top speaker 70 and one bottom speaker 72. In the preferred embodiment, speakers 70 and 72 are 18" in diameter and are woofer-type speakers.

The specific vibration chamber depicted in FIG. 2 can hold either one or two printed circuit boards 74 of dimensions 9" by 18", and with boards of this size the distance between the two speakers 70 and 72 would preferably be between 6" and 10". Alternatively, the preferred embodiment as illustrated can hold one circuit board of 18"×18". Since the speakers are symmetrically spaced from top to bottom, i.e., the printed circuit board 74 is equidistant from each speaker in the preferred embodiment, so that the distance between each of the speakers 70 and 72 and the printed circuit board 74 is between 3–5". In this range of distances, maximum vibration force can be achieved on printed circuit cards of this size without destroying the electrical and electronic components. If the distance between the speakers 70 and 72 and the printed circuit board 74 is decreased to less than 3", the vibration forces increase at a logarithmic rate. If the distance between the speakers 70 and 72 and the printed circuit board 74 remain 3" or greater, then the vibration forces remain approximately linear and are inversely proportional to the distance. At this recommended 3–5" distance between each speaker 70 or 72 and the printed circuit board 74, the area of effective acoustical vibration is about 2" beyond the diameter of each speaker. Since 18" speakers are used in the preferred embodiment, the area of effective vibration is about 22" in diameter.

To construct a vibration chamber 10 of the proper size for the illustrated embodiment of FIG. 2, the outer dimensions of the chamber are 31½" in length by 40¼" in width, by 49" in height. The material of the vibration chamber cabinet, consisting in part of the vertical and horizontal walls 12, 14, 16, and 18, is as follows: the outer layer is wood having two plys, 1 3/16" thick, overall. Inside the wood layer is a layer of sound absorbing and sound insulating material 20. Such material is commercially available, such as that sold by Soundcoat under the Trademark "Soundmat PB," which consists of three layers which are 2" in overall thickness. There are two soundabsorbing layers which sandwich an inner sound-barrier layer. The effect of using Soundmat PB with the outer wood cabinet is that there are no resonant frequencies of acoustic vibration set up inside the vibration chamber 10 (any resonances that might exist will be so minute as to be negligible).

Another feature of the construction of the illustrated embodiment of the vibration chamber 10 in FIG. 2 are the two openings 58 on the front and rear surfaces of the vibration chamber. The front and rear openings 58 allow printed circuit boards 74 to enter and exit the vibration chamber 10, before and after being tested, respectively. These openings 58 cannot merely remain open during vibration testing, but they must be covered by either a door, or some other type of material. In the illustrated embodiment of FIG. 2, each opening 58 is covered by three plastic flaps 76. These plastic flaps are made of anti-static plastic, approximately 80 mils in thickness, and have about a 1½" air gap between them. These anti-static plastic flaps 76 are flexible enough so that they are pushed out of the way by a printed circuit board which is either being inserted or removed from the vibration chamber. The anti-static plastic flaps 76 also have sound deadening characteristics, so that they help to significantly reduce the audible sounds that would otherwise emanate from the vibration chamber 10 through the openings 58.

Figure 3:
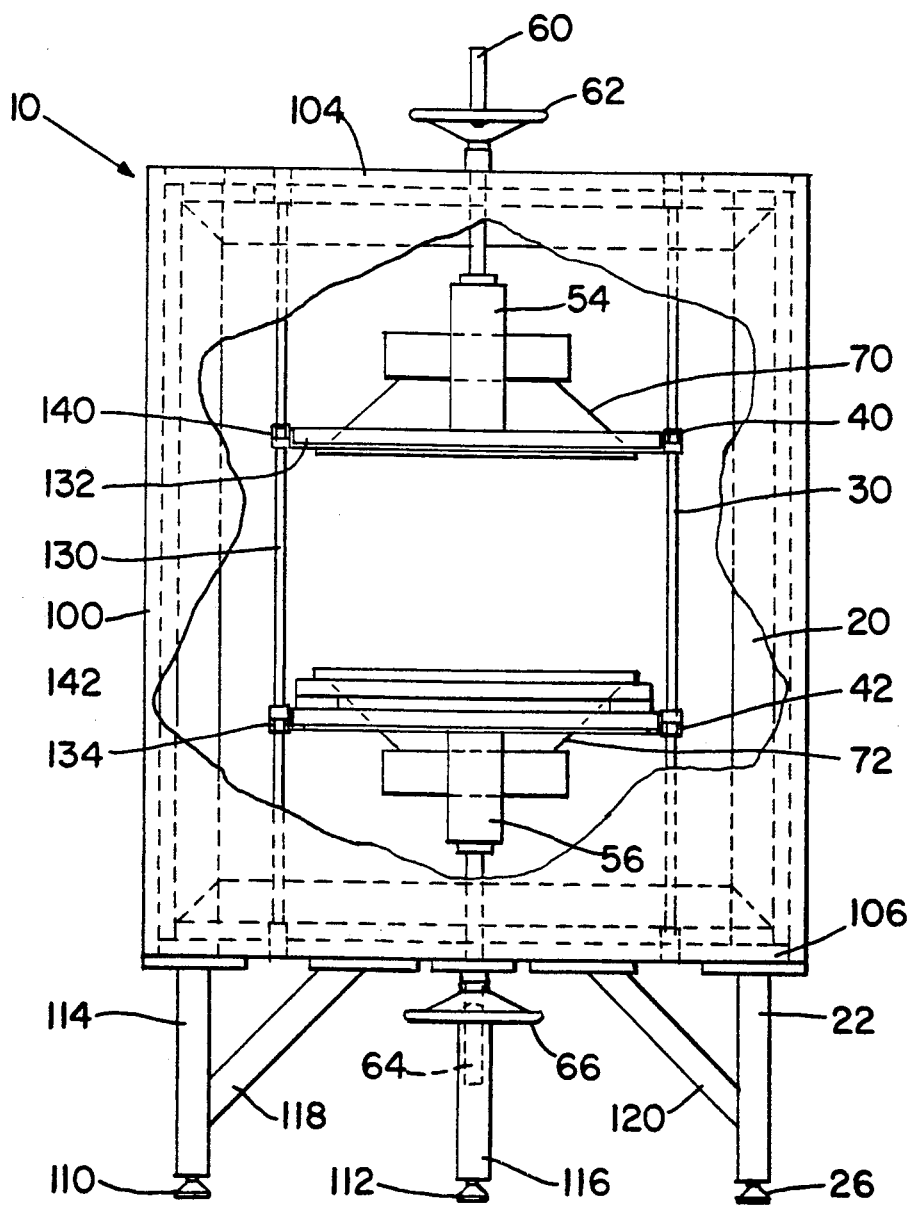
FIG. 3 is a side elevational view partially in cross-section of the vibration chamber depicted in FIG. 2

A side elevation view of the vibration chamber 10 depicted in FIG. 3 shows many of the same features and construction techniques as in FIG. 2. There are two vertical walls 100 and 102, two horizontal walls 104 and 106, and the interior surfaces of these walls are, again, lined by sound deadening and insulating material 20. As before, there are vertical support legs 22, 116, and 114, leveling feet, 26, 110, and 112, as well as cross braces 118 and 120. The speakers 70 and 72 are mounted on their respective speaker support frames 54 and 56, as well as their respective horizontal speaker supports 132 and 134. The horizontal speaker supports are attached to speaker guides 40, 42, 140, 142 which in turn slide up and down the vertical guide rails 30 and 130. The speaker support frames 54 and 56 are, again, attached to the top and bottom jack screws 60 and 64, which are in turn actuated by the jack screw adjustments 62 and 66.

Figure 4:
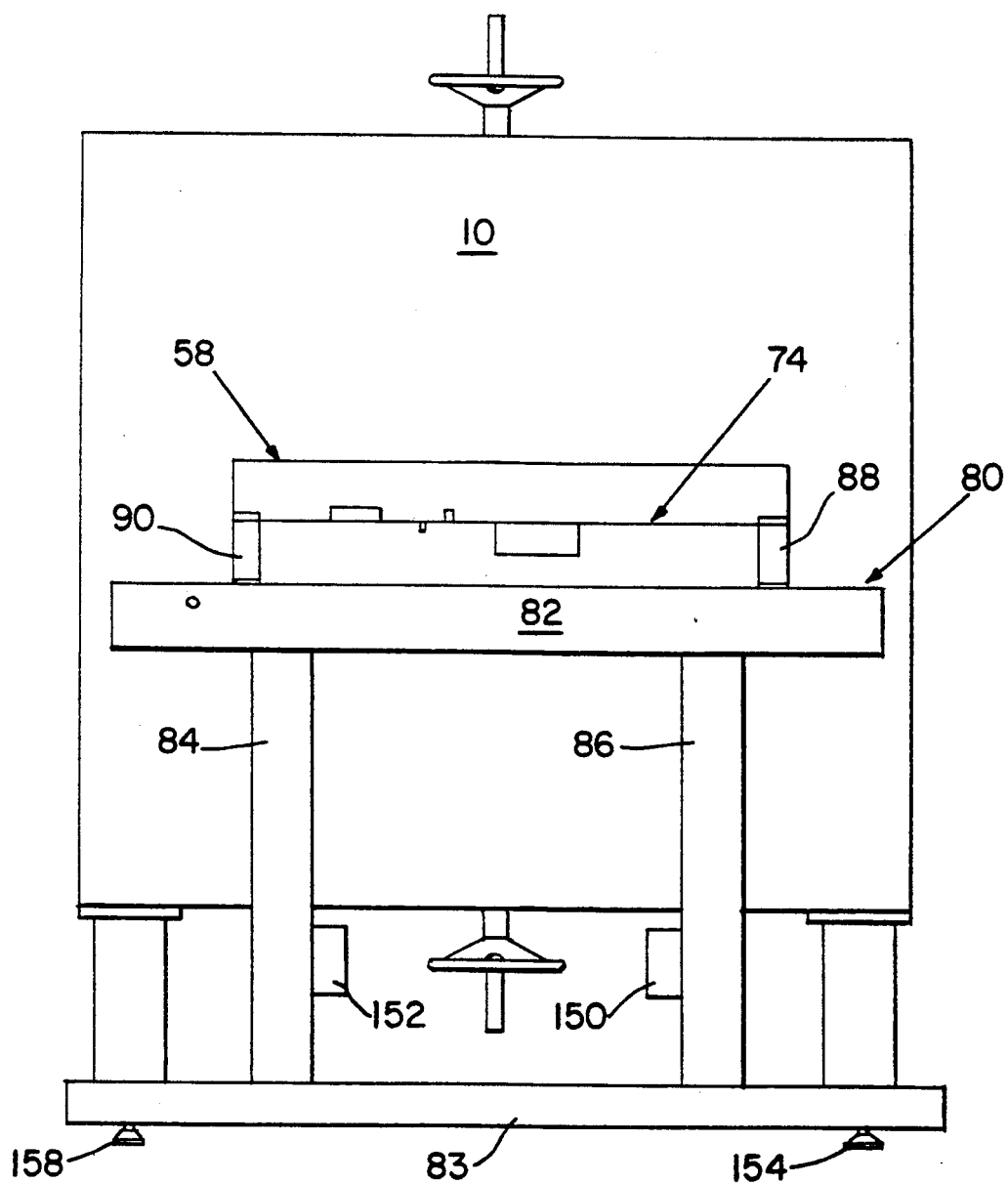
FIG. 4 is a front elevational view similar to FIG. 2 but depicting only exterior features of the vibration chamber.
Figure 5:
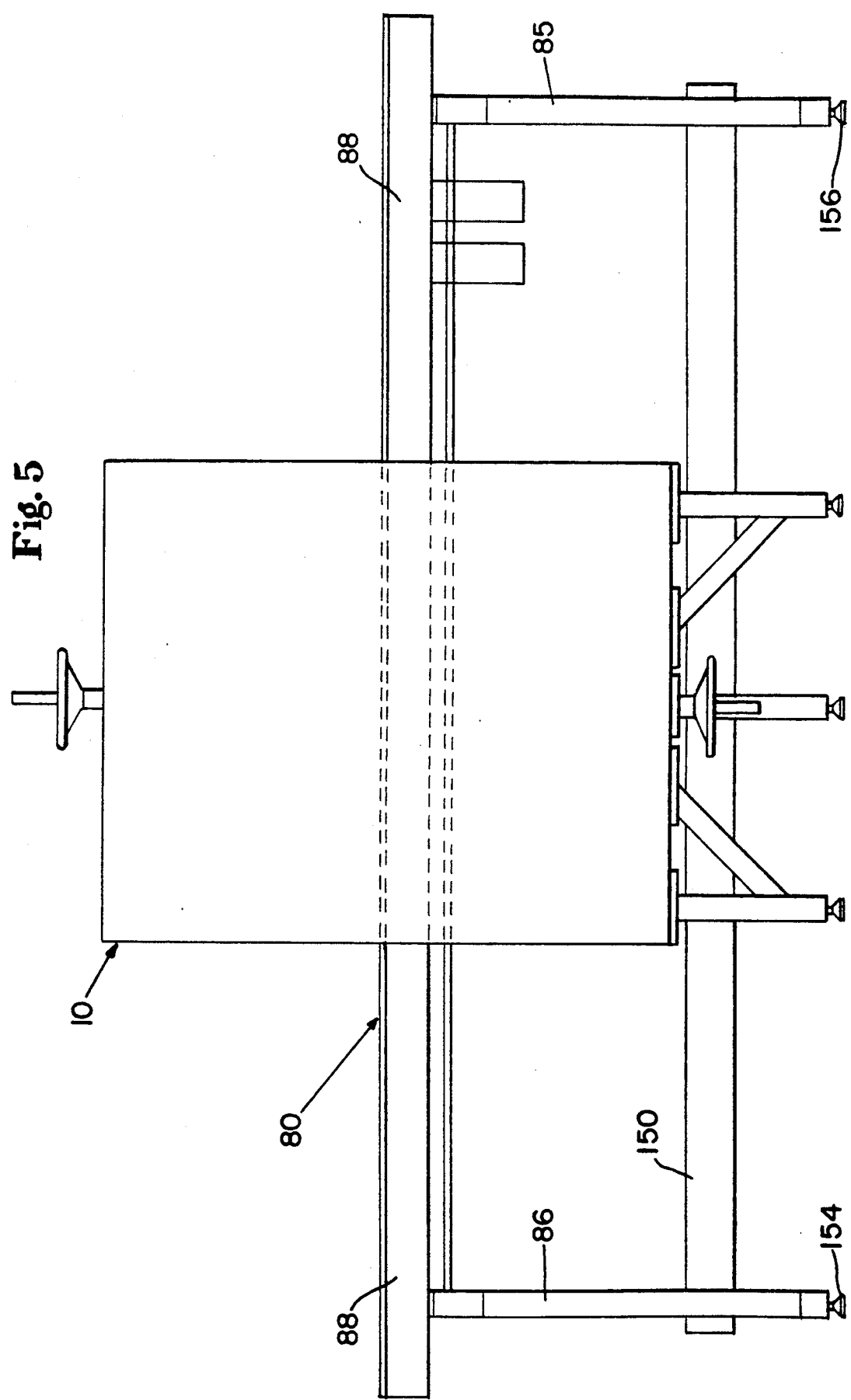
FIG. 5 is a side elevational view of the vibration chamber and conveyor system depicted in FIG. 4.

As illustrated in FIG. 4, a conveyor system 80 can be used to insert printed circuit boards 74 into the vibration chamber 10, to hold such printed circuit boards in place through vibration testing or screening, and then to extract the printed circuit boards from the vibration chamber 10 after the test or screening is completed. Such conveyor systems are commercially available including a roller conveyor manufactured by Conveyall for use with printed circuit boards. It is important that such roller conveyor system 80 be "electrostatic discharge safe". A conveyor that is electrostatic discharge safe can handle printed circuit boards that are directly touching it because the conveyor is made of parts that are coated with electrically conductive material, and which will not allow any type of electrostatic discharge to destroy components on the printed circuit boards. FIGS. 4 and 5 depict the conveyor system used in the preferred embodiment. The construction of the conveyor 80 is relatively simple: there are conveyor system horizontal supports 82 and 83, which are attached to leveling feet 154, 156, and 158. Attached to the conveyor system horizontal supports are conveyor system vertical supports 84, 85, and 86. Attached to these conveyor system vertical supports are two rather long conveyor cross braces 150 and 152. The conveyor system has two roller assemblies: a fixed roller assembly 88, and an adjustable roller assembly 90. The conveyor system adjustable roller assembly 90 can be moved along the horizontal plane so that printed circuit boards 74 of different width can be accommodated by this single conveyor assembly 80. While not shown in detail in FIG. 4, a conveyor system 80 has upper and lower rollers as part of the fixed and adjustable roller assemblies 88 and 90 which form a path between which the printed circuit boards 74 travel. As can be seen in FIGS. 4 and 5, the two roller assemblies 88 and 90 form a path all the way through the vibration chamber 10 through the openings 58.

Figure 7:
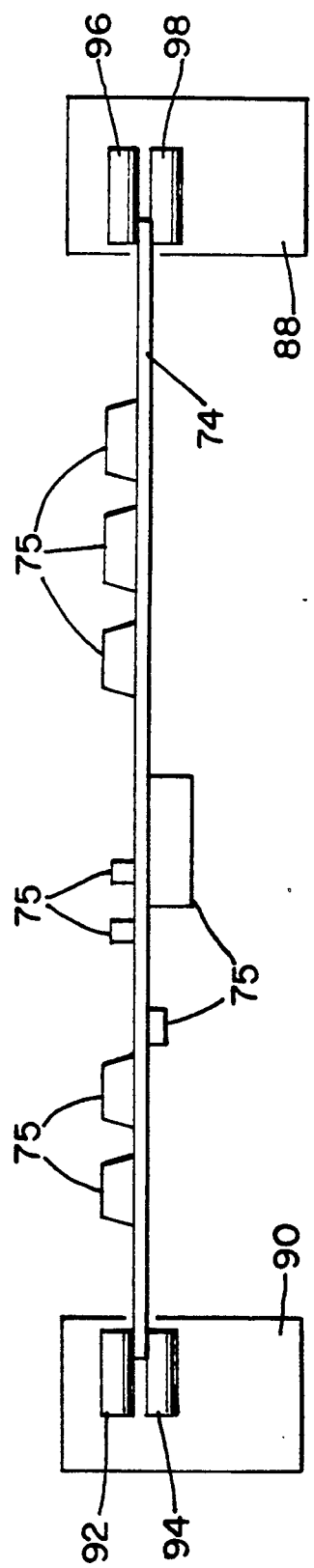
FIG. 7 is cross-section elevational view of the details of the adjustable roller conveyor with a printed circuit board in place.

The conveyor system 80 confines the printed circuit board 74 only along its edges in the preferred embodiment. The printed circuit board 74 is held in place inside the vibration chamber 10 by the rollers 92, 94, 96 and 98, as shown in FIG. 7. The sound waves which are generated above and below the printed circuit board 74 tend to flex the printed circuit board in the vertical axis, which is called the axis of vibration. The roller conveyor assembly 80 of the preferred embodiment allows the printed circuit board 74 to flex freely up and down in the axis of vibration, thereby allowing effective testing or screening using a profile of random vibrations. As long as the components 75 of the printed circuit board 74 are not located too close to the edge of the board, the rollers 92, 94, 96, 98 will not interfere with such components 75.

Figure 6:
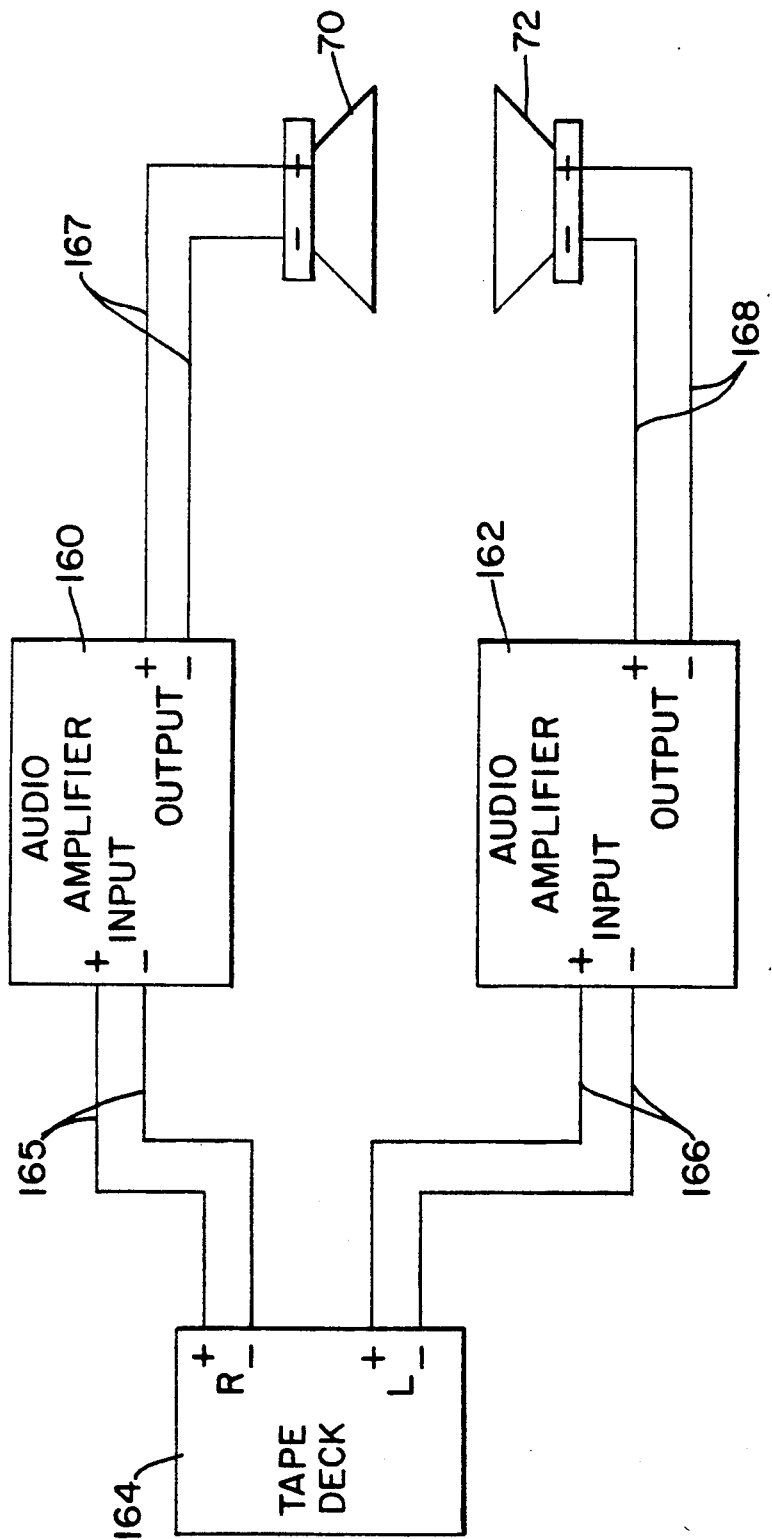
FIG. 6 is a block diagram of the electrical connections required with a vibration chamber in accordance with the present invention.

The electrical equipment of the vibration chamber system is depicted in block diagram form in FIG. 6. The top speaker 70, is connected to a 1000 watt audio amplifier 160 by use of a pair of wires 167. The polarity of the wiring is very important; the "plus" output of the 1000 watt amplifier 160 is connected to the "plus" input of the top speaker 70.

The bottom speaker 72 is connected to a second 1000 watt audio amplifier 162 by use of a pair of wires 168. Again, polarity is critical, for in the case of the bottom speaker 72, the "plus" output of the 1000 watt amplifier 162 must be connected to the "minus" input of the bottom speaker 72. In this way the top speaker 70 and bottom speaker 72 will operate 180° out-of-phase, and the two speakers will operate in a "push-pull" arrangement (where the speakers face one another and are electrically connected 180° out-of-phase). This creates the situation where air is being either pushed up or pulled down by both speakers simultaneously as each component of each sine wave passes through the speakers.

Figure 1:
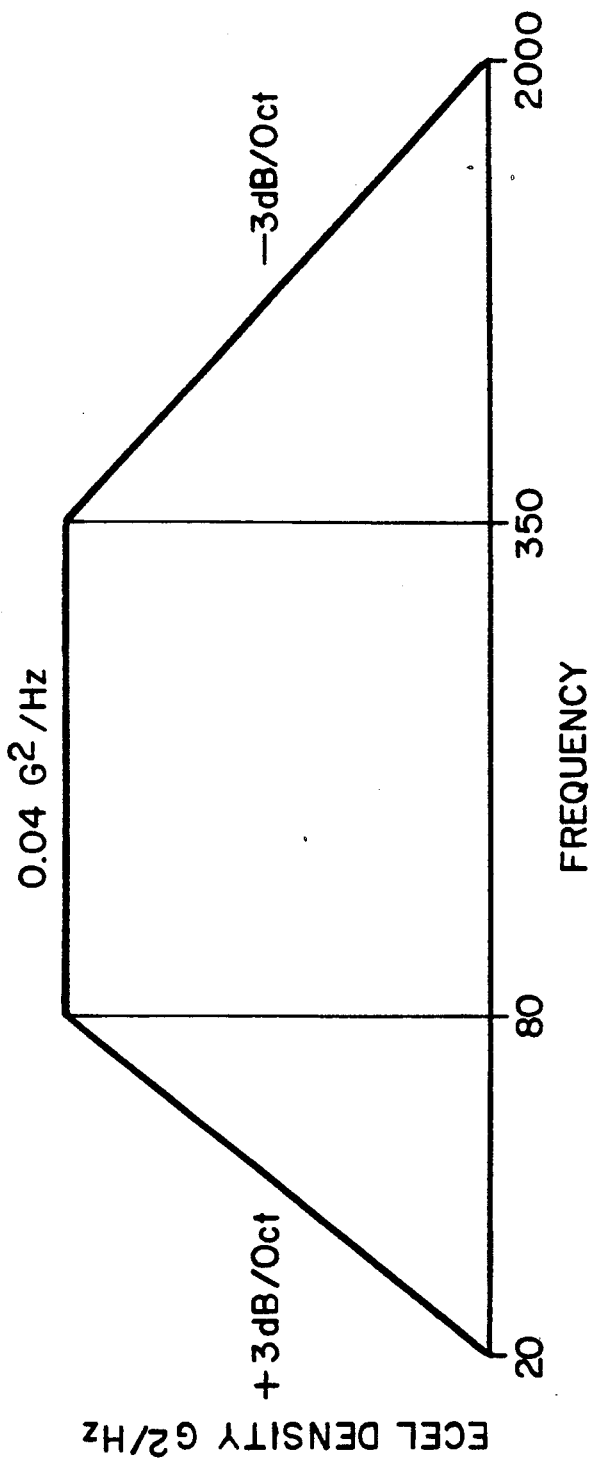
FIG. 1 is a curve for a typical random vibration profile, wherein the acceleration density is plotted against frequency of vibration. From the area under the curve, the Power Spectral density is calculated, in $g_{rms}$.

The actual volume of sound produced by the speakers 70 and 72 in decibels is not the most important concept of this invention. A more important concept of this invention is the magnitude of g-forces that are produced at the printed circuit board 74 itself. While the output of the speakers is a constant, the g-forces produced on the printed circuit board 74 are variable depending upon the distance the speakers 70 and 72 are located from the printed circuit board 74. As discussed above, in the preferred embodiment, the speakers 70 and 72 are normally placed at a distance of from 3-5" from the printed circuit board 74. Under these conditions, a random vibration profile can be generated to impart a total of approximately 6 g's$_{rms}$ onto the printed circuit board under test over the frequency range of 20 Hz to 2000 Hz (as depicted in FIG. 1).

The random noise profile must be created or at least available to drive the speakers 70 and 72 and the 1000 watt amplifiers 160 and 162. In FIG. 6 a tape deck 164 is used to drive the two 1000 watt amplifiers 160 and 162. The top speaker's amplifier 160 is connected to the right channel of the tape deck 164 using a pair of wires 165. Polarity is once again important, and the "plus" output of the tape deck 164 must be connected to the "plus" input of the 1000 watt amplifier 160. The left channel of the tape deck 164 is connected to the bottom speaker's amplifier 162 using a pair of wires 166. As before, polarity must be observed, with the "plus" left output of the tape deck 164 connected to the "plus" input of the bottom speaker's amplifier 162. The maximum length of a test for a given printed circuit board 74 would be 15 minutes.

If the profile for the random vibration has not been yet created, then a tape deck 164 cannot be used as shown in FIG. 6. In place of the tape deck 164, a vibration controller must be used instead. The vibration controller has the capability of simultaneously generating many frequencies in the frequency range of interest, which is 20 Hertz to 2,000 Hertz in the preferred embodiment. The vibration controller also has the capability of notching out certain frequencies which are undesirable in the given application. Such vibration controllers are commercially available, including one manufactured by Gen Rad, under Gen Rad's part number GR2511.

In the acoustic vibration chamber application, the vibration controller will set up a profile of random noise which will include all frequencies between 20 and 2,000 Hz except for certain resonant frequencies of the printed circuit board 74 which must be notched out of the program of random noise. Such resonant frequencies can be determined by the following method: accelerometers should be attached to the leads of all components that are sticking out of the printed circuit board. Such accelerometers must be monitored while the entire printed circuit board assembly is vibrated gently at frequencies between 20 and 2,000 Hz. Starting at 20 Hz, the frequency is controlled very tightly and is slowly ramped up to 2,000 Hz. All during this time, each accelerometer is monitored for excess g forces. After each sweep of frequency, the g force of vibration is increased incrementally, and then a new frequency sweep is initiated. Eventually, certain accelerometers will generate large g forces at given frequencies. Once those frequencies are determined, they can be notched out of the profile of random vibration that is to take place on the entire printed circuit board assembly for its testing or screening program. Since the notching out of the printed circuit board's 74 resonant frequencies is critical, it can be seen that the profile of random noise must be tailored to each type of printed circuit board that is to be tested or screened. Such notching out must be accomplished for the purpose of allowing the entire printed circuit board to be harshly vibrated such that the actual solder connections can be mechanically tested, without in the meantime exposing the leads of the individual components to certain breakdown.

Figure 8:
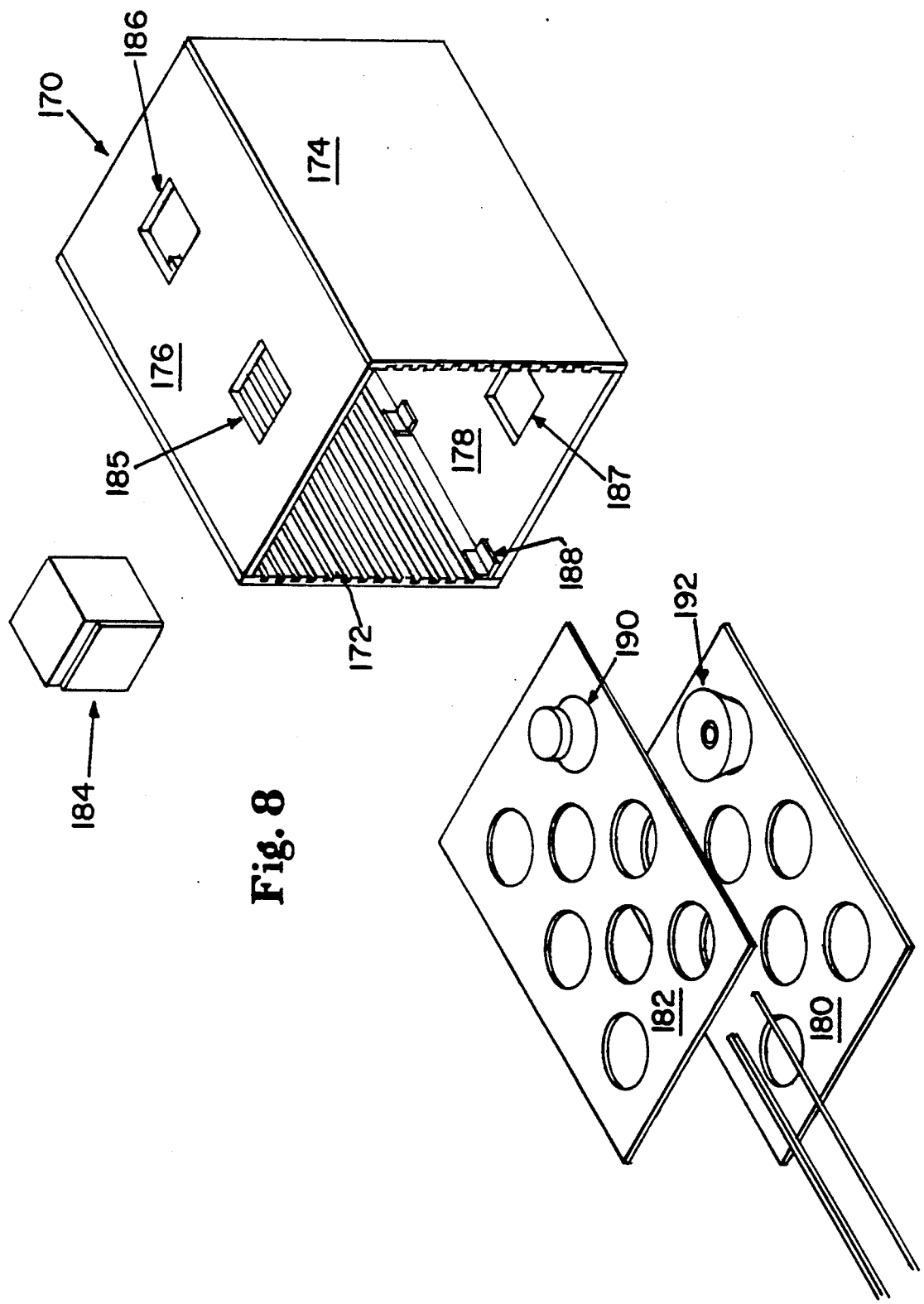
FIG. 8 is an oblique view of a second embodiment of the invention which uses multiple speakers in both top and bottom assemblies.

Another embodiment of the present invention which uses multiple speakers on both the top and bottom is illustrated in FIG. 8. In situations where a larger acoustic vibration chamber 170 is required, it is necessary to use more than one speaker on each of the top and bottom locations in order to vibrate larger or more numerous printed circuit boards. This acoustic vibration chamber 170 is constructed of vertical walls 172 and 174, and horizontal walls 176 and 178, which are held together by steel L brackets 188. The material used for the horizontal and vertical walls is ⅝" plywood. The vertical walls 172 and 174 are slotted on their interior surfaces in order to allow the shelves that hold the speakers 180 and 182 to be slid into position at different distances from the printed circuit boards. Each horizontal speaker support shelf 180 and 182 has eight large holes in it in order to hold the speakers 190 and 192. Speakers 190 and 192 are axially aligned and face each other, and the printed circuit boards that are to be tested or screened are placed in position between the speakers.

There are eight top speakers 190 which are all wired in parallel, and are in phase with one another. There are also eight bottom speakers 192 which are wired in parallel, and are in phase with one another. As a group, a top speakers 190 are wired 180° out of phase with the bottom speakers as a group 192.

The horizontal walls 176 and 178 have two large openings in them such as illustrated at 185 and 186. These openings are to allow a certain amount of air to be vented from the back of the speakers, so as to keep the back pressure on the speakers from being excessive. The air behind the speakers is not merely vented to atmosphere, however, but instead must first pass through a baffle chamber 184. The baffle chambers 184 are located on top of each of the two openings 185 and 186 that are on the upper horizontal wall 176, and are also located just below the two openings one of which is illustrated at 187, in the lower horizontal wall 178. The baffle chambers 184 are constructed of plywood on their exterior surfaces. The interior of the baffle chambers 184 consist of layers of ⅝" plywood and ¼" sound deadening foam. In effect, the baffle chambers 184 act as sound mufflers.

In summary, numerous benefits have been described which result from employing the concepts of the present invention. The push-pull arrangement of the top and bottom speakers 70 and 72 provides the maximum amount of vibration force available from any two speakers in an acoustical vibration system. This is so because the speakers are wired out-of-phase, thereby creating complementary push-pull air vibrations, instead of both speakers attempting to push air out simultaneously, thereby interfering with each other's vibratory effect on the device under test. The use of top and bottom speakers also insures that both the top and bottom of the printed circuit board 74 will receive equal vibration energy. The use of speaker-height adjustments makes it possible to impart the maximum g-forces of random vibration energy onto the device under test while using only one vibration chamber for several types and sizes of printed circuit boards. Furthermore, the combination of a roller conveyor system 80 of the type described in the preferred embodiment makes it possible to perform random vibration screening for printed circuit boards in a production environment.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A vibration chamber comprising:
   (a) a housing, said housing having interior and exterior surfaces;
   (b) a pair of speakers supported by said housing, said speakers facing one another and arranged in a push-pull configuration;
   (c) means for positioning a test part between said speakers; and
   (d) means for delivering electrical energy to said speakers so as to create acoustic vibrations by said speakers and impart said vibrations upon said part, said delivering means driving said pair of speakers in a push-pull manner throughout a wide range of varying frequencies.

2. A vibration chamber as recited in claim 1, wherein said speakers are axially aligned.

3. A vibration chamber as recited in claim 2, further comprising a plurality of pairs of speakers in a push-pull configuration.

4. A vibration chamber as recited in claim 2, further comprising layers of sound deadening and sound insulating material located on the interior surfaces of said housing, said layer of sound deadening and sound insulating material having the propensity to isolate the vibration chamber interior from the ambient surroundings.

5. A vibration chamber as recited in claim 2, further comprising conveying means for moving components into and from said vibration chamber through openings in said housing, said conveying means configured so as to restrict the movement of only the edges of said components in the axis of vibration.

6. A vibration chamber as recited in claim 2, including means for producing said wide range of frequencies in a random manner.

7. A vibration chamber as recited in claim 2, wherein said speakers are facing one another in the vertical plane, such that the top speaker is facing down, and the bottom speaker is facing up.

8. A vibration chamber as recited in claim 1, wherein said speakers are facing one another in the vertical plane, further comprising a plurality of top speakers electrically connected in parallel, and a second plurality of bottom speakers electrically connected in parallel, with said two groups of speakers arranged in a push-pull configuration.

9. A vibration chamber as recited in claim 2, wherein the position of said speakers is adjustable so that said speakers may be located nearer or further from said test part, as required to impart optimum acoustic vibrations upon said test part.

10. A vibration chamber as recited in claim 2, further including a test part, and wherein the size in diameter of said speakers is large enough to vibrate the entire surface area of said test part substantially uniformly.

11. A vibration chamber as recited in claim 2, wherein the position of said speakers is adjustable in the range of 3" to 5" distance between each speaker and said test part's surface.

12. A vibration chamber as recited in claim 5, further comprising means for attenuating sound emanating from within the vibration chamber, such sound exiting at said openings, but which means allow test parts to pass through said openings.

13. A vibration chamber as recited in claim 6, wherein said means for delivering electrical energy consists of audio power amplifiers driving said speakers, and a vibration controller driving said audio power amplifiers.

14. A vibration chamber as recited in claim 6, wherein said means for delivering electrical energy consists of audio power amplifiers driving said speakers, and a tape deck driving said audio power amplifiers.

15. A vibration chamber as recited in claim 14, wherein the frequency response range of said tape deck is 20 Hz to 2,000 Hz, inclusive.

16. A vibration chamber as recited in claim 12, wherein said means for attenuating sound consists of sound insulating and sound deadening material covering said openings.

17. A method of testing or screening parts in a vibration chamber which comprises the steps of:
   (a) placing at least one test part inside a vibration chamber;
   (b) inducing vibrations in said at least one test part by use of sound waves emanating from a pair of speakers arranged in a push-pull configuration and located inside said vibration chamber, said speakers being driven by a means for delivering electrical energy in a push-pull manner through a selected frequency; and
   (c) varying said selected frequency according to a profile of vibration through a wide range of frequencies, for a given type of said test part.

18. The method as defined by claim 17, wherein said step of placing said test part inside the vibration chamber is carried out with a conveying system.

19. The method as defined by claim 17, wherein said step of inducing vibrations in said test part is carried out by said speakers which are adjustable in distance from said test part, and said speakers are sized in diameter so as to induce said vibrations all along the surface area of said test part(s).

20. The method as defined by claim 17, which further comprises the step of:
   (d) removing said test part from the interior of the vibration chamber once said testing or screening procedure is completed.

21. The method as defined by claim 20, wherein said step of removing said test part from the vibration chamber is carried out with a conveying system.

22. A method of testing or screening parts in a vibration chamber, which comrpises the steps of:
   (a) placing at least one test part inside a vibration chamber;
   (b) inducing low amplitude vibrations in said at least one test part by use of sound waves emanating from a pair of speakers arranged in a push-pull configuration and located inside said vibration chamber, said speakers being driven by a means for delivering electrical energy in a push-pull manner through a wide range of frequencies, in which the frequencies of said means for delivering electrical energy ramp up from low frequency to high frequency over time; and measuring the forces on individual components of said at least one test part at specific frequencies in order to determine their frequency of resonance;
   (c) creating a profile of vibration through said wide range of frequencies for a given type of said test part, including notching out all said resonant frequencies from said profile of vibration; and
   (d) inducing high amplitude vibrations in said at least one test part by use of sound waves emanating from said pair of speakers, said speakers being driven by said means for delivering electrical energy through a wide range of frequencies of said profile of vibration.

* * * * *